United States Patent
Krastev

(10) Patent No.: US 9,326,828 B2
(45) Date of Patent: May 3, 2016

(54) DENTAL DEVICE

(71) Applicant: Pavel Krastev, New Hyde Park, NY (US)

(72) Inventor: Pavel Krastev, New Hyde Park, NY (US)

(*) Notice: Subject to any disclaimer, the term of this patent is extended or adjusted under 35 U.S.C. 154(b) by 0 days.

(21) Appl. No.: 14/309,391

(22) Filed: Jun. 19, 2014

(65) Prior Publication Data

US 2015/0366633 A1 Dec. 24, 2015

(51) Int. Cl.
*A61C 3/04* (2006.01)
*A61C 5/04* (2006.01)

(52) U.S. Cl.
CPC .... *A61C 3/04* (2013.01); *A61C 5/04* (2013.01)

(58) Field of Classification Search
CPC ............. A61C 3/04; A61C 19/02; A61C 5/04
USPC .................................................. 433/224, 229
See application file for complete search history.

(56) References Cited

U.S. PATENT DOCUMENTS

| | | | |
|---|---|---|---|
| 941,718 A | 11/1909 | Koons | |
| 1,451,806 A * | 4/1923 | Baldridge | A61C 3/04 206/369 |
| 1,684,417 A * | 9/1928 | Silberman | A61C 19/02 206/229 |
| 1,915,958 A * | 6/1933 | Skirrow | B60N 3/007 108/44 |
| 1,973,222 A * | 9/1934 | Moore | B65D 85/24 206/369 |
| D170,651 S * | 10/1953 | Palczewski | 206/370 |
| 3,163,287 A * | 12/1964 | Barnett | A47G 23/0641 108/44 |
| 3,358,826 A * | 12/1967 | Siegel | A61C 5/025 206/368 |
| 3,379,315 A * | 4/1968 | Broadwin | 211/72 |
| 3,451,133 A | 6/1969 | Etal | |
| 3,497,057 A * | 2/1970 | Traner et al. | 206/730 |
| 3,532,221 A * | 10/1970 | Kaluhiokalani | A45D 44/02 108/26 |
| 3,554,284 A * | 1/1971 | Nystrom | 166/254.2 |
| 3,643,812 A * | 2/1972 | Mander | B01L 9/06 206/443 |
| 3,938,253 A * | 2/1976 | Barnard | A61C 19/00 433/75 |
| D240,537 S * | 7/1976 | Sronce | D24/230 |
| 4,182,040 A * | 1/1980 | Bechtold, Jr. | A61C 5/025 433/75 |
| 4,184,251 A * | 1/1980 | Kuboki | A61C 13/12 433/163 |
| 4,191,291 A * | 3/1980 | Brown | B65D 1/36 206/369 |
| 4,232,784 A * | 11/1980 | Hesselgren | 206/210 |
| 4,293,074 A * | 10/1981 | Dunsky | A61C 19/02 206/369 |
| 4,327,060 A * | 4/1982 | Nisii | A61C 3/04 206/210 |
| 4,353,694 A | 10/1982 | Pelerin | |

(Continued)

FOREIGN PATENT DOCUMENTS

| | | |
|---|---|---|
| DE | 20102483 | 9/2002 |
| EP | 1417937 A1 | 5/2004 |

(Continued)

OTHER PUBLICATIONS

Patterson Endodontic Organizers—Gutta Percha Box Micro—Patterson Dental Design, Patterson Dental, No Date.

(Continued)

*Primary Examiner* — Cris L Rodriguez
*Assistant Examiner* — Hao D Mai
(74) *Attorney, Agent, or Firm* — Kane Kessler, P.C.; Paul E. Szabo

(57) ABSTRACT

A holder for dental workpieces that are associated in a one to one relationship with the canals of a tooth has receptacles for temporarily storing the workpieces while the workpieces are not in the tooth. The receptacles are sufficient in number to store the workpieces with a single workpiece in each receptacle. The receptacles are arranged in a pattern that corresponds to the canal pattern in the tooth.

12 Claims, 7 Drawing Sheets

(56) References Cited

U.S. PATENT DOCUMENTS

| | | | | |
|---|---|---|---|---|
| 4,382,788 A | * | 5/1983 | Pelerin | 433/77 |
| 4,482,522 A | * | 11/1984 | Baudisch et al. | 422/566 |
| 4,828,113 A | * | 5/1989 | Friedland | A61B 19/44 |
| | | | | 206/369 |
| 5,000,713 A | * | 3/1991 | Cheng | 446/120 |
| 5,031,768 A | * | 7/1991 | Fischer | A61B 19/0264 |
| | | | | 206/364 |
| 5,036,989 A | * | 8/1991 | Carilli | 211/74 |
| 5,071,002 A | * | 12/1991 | Bradley | 206/217 |
| 5,071,346 A | | 12/1991 | Domaas | |
| 5,174,453 A | * | 12/1992 | Stoeffler | A61B 19/0256 |
| | | | | 206/370 |
| D334,815 S | * | 4/1993 | Bunger | D21/501 |
| 5,279,800 A | * | 1/1994 | Berry, Jr. | A61L 2/26 |
| | | | | 206/363 |
| 5,285,907 A | * | 2/1994 | Franchere et al. | 211/74 |
| 5,289,919 A | * | 3/1994 | Fischer | A61C 19/02 |
| | | | | 206/366 |
| 5,358,112 A | * | 10/1994 | Gardner | A61C 3/04 |
| | | | | 206/369 |
| 5,507,643 A | * | 4/1996 | Klein | A61C 13/30 |
| | | | | 433/141 |
| 5,692,609 A | * | 12/1997 | Lin | A61C 19/02 |
| | | | | 206/368 |
| 5,743,734 A | * | 4/1998 | Heath et al. | 433/77 |
| 5,752,598 A | * | 5/1998 | Zdarsky | 206/63.5 |
| 5,829,590 A | * | 11/1998 | Klein | A61C 19/02 |
| | | | | 206/369 |
| 5,967,778 A | * | 10/1999 | Riitano | A61C 19/002 |
| | | | | 206/366 |
| 6,206,192 B1 | * | 3/2001 | Winstead | A61C 19/02 |
| | | | | 206/369 |
| 6,213,771 B1 | * | 4/2001 | Fischer | 433/75 |
| 6,592,092 B2 | * | 7/2003 | Stahlberg | 248/311.3 |
| 6,764,306 B1 | * | 7/2004 | DiMarino | A61C 3/02 |
| | | | | 206/369 |
| 8,191,718 B2 | | 6/2012 | Hovatter | |
| 2003/0186188 A1 | * | 10/2003 | Tinnin | 433/77 |
| 2005/0016886 A1 | * | 1/2005 | Riley | 206/438 |
| 2005/0064367 A1 | * | 3/2005 | Discko | A61C 19/006 |
| | | | | 433/80 |
| 2006/0223034 A1 | * | 10/2006 | Fischer | A61C 5/023 |
| | | | | 433/220 |
| 2006/0223035 A1 | * | 10/2006 | Fischer | A61C 5/023 |
| | | | | 433/220 |
| 2012/0273446 A1 | | 11/2012 | Moore | |

FOREIGN PATENT DOCUMENTS

| | | |
|---|---|---|
| FR | 2580490 | 10/1986 |
| WO | 9806351 | 2/1998 |

OTHER PUBLICATIONS

Helio Endo Organizer, Diadent, Interdent Dental and Medical Supply, No Date.
Endo Container, Smart Practice, No Date.
Endo Case H, Equipd Professional Dental Supplies, Sep. 12, 2011.
Dental Bur Stand/Block, Aliexpress.com, No Date.

\* cited by examiner

DENTAL DEVICE

TECHNICAL FIELD

The present invention relates to endodontic therapy, and more specifically to a device that is helpful for the organization of materials used during the endodontic treatment of teeth. The present invention allows the transfer of master cones of gutta percha, and similar materials (dental workpieces) from a tooth to the device, and then back to the tooth. This can be done during the obturation phase of endodontic treatment.

BACKGROUND OF THE INVENTION

Human tooth anatomy varies externally and internally. However, there are general anatomical features and patterns which are relatively consistent, such as the general shape of teeth and the general distribution of the canals found within a tooth. The space the dental pulp occupies in the coronal portion of a tooth is known as the pulp chamber. From the coronal chamber, the pulp tissue enters each tooth root through an orifice and travels in an apical direction further into the canal space, until it exits the end of the root through the apical foramina. This apical terminus is also known as the apex. Within the apical portion of a root is housed the apical constriction. The apical constriction is the narrowest portion of the root terminus. In a properly treated root canalled tooth, the apical constriction must be gagged and properly scaled.

There are many conditions which can lead to pulpal disease. when pulpal disease is diagnosed, endodontic treatment becomes necessary. Endodontic treatment is commonly known as root canal therapy. When caries for example goes untreated, it eventually begins to communicate with the pulpal tissues and leads to inflammation of the pulp. Such inflammation is known as pulpitis. Pulpitis causes severe pain and warrants endodontic intervention. When pulpitis goes untreated, the pulp tissues become necrotic (dead) in a given tooth and its associated canal systems. The residual necrotic debris that resides in the previously occupied pulpal space begins to communicate with the bone housing the tooth. This process leads to bone destruction, also known as peri-apical pathology.

The treatment of peri-apical pathology is accomplished via root canal therapy. When root canal therapy is properly carried out, the pathology will likely heal, thus saving the tooth in question. When pulpal disease goes untreated, further complications can arise. Such complications can be abscesses or cellulitis, and can potentially spread to other portions of the human body. Although it is rare, certain complications can be fatal.

When the dental specialist is faced with a patient with a diseased pulp, endodontic therapy is initiated by isolating the tooth with a rubber dam, and gaining access to the pulp by drilling through the enamel and dentin of a given tooth and reaching the pulp chamber. The next step involves locating the orifice of each canal within the particular tooth. Then, stainless steel files or nickel titanium files are used to negotiate each orifice. Following negotiation of the orifices, the working length of each canal system is established. This three dimensional complex is cleaned and shaped using various methods. Hand files of all sorts are available, as well as rotary files to clean and shape the canals of a given tooth.

Instrumenting to the proper working length is essential for endodontic success. Most often, digital apex locators are used along with x-rays to determine the working length of each canal. Apex locators measure where the apical constriction is located for each canal. The apical constriction is the location to which canal preparation should be carried.

Following and during the cleaning and shaping phase, the canals are treated with various chemical agents to destroy any left over microorganisms (detoxify). Examples of such agents are Sodium Hypochlorite (NaOCl) and EDTA.

The next step is canal obturation, or sealing of the previously instrumented canal in the tooth. The goal of obturation is to close and seal the apical constriction, and to three dimensionally fill the canal space preceding the apical constriction. Paste fillers and silver points were used in the past, but gutta percha is the standard of care used today. Gutta percha comes in thin cones of varying colors, tapers and sizes. The upper ends of the gutta percha are usually color coded to correspond to their respective sizes. Gutta percha can be thermo softened and injected into a given canal once the apical constriction has been sealed with the master cone of gutta percha. Some examples of devices used to inject gutta percha are the Obtura-II from Obtura-Spartan Endodontics, and the Calamus units of Dentsply International. Gutta percha can also be delivered using a carrier based device. Examples are Thermafil from Dentsply International, One fill from US Endodontics, and Soft-Core from Sybron Dental Specialties. Regardless of the method used, proper sealing of the root is imperative.

Following instrumentation of a given root to a given size file as described above, the canal is detoxified. A single master cone of gutta percha is placed in each respective canal. The gutta percha selected corresponds to the size of the last file used to carry out the instrumentation phase.

In multi rooted teeth, it is not uncommon to have canals instrumented to varying sizes. it is also usual that the working depth as recorded from a reference point of the coronal aspect of a tooth will vary in respective roots. Thus, different canals in a given tooth can have different working lengths and can be instrumented to different size final files. This will necessitate filling the different canals with different sized master cones.

In general, instruments and gutta percha and paper points can be color coded to correspond to each other. Paper points are typically used to dry canals prior to obturation. Paper points are also often used to carry the sealer cement into respective canals prior to inserting the master cone of gutta percha. Typically, after the master cones of gutta percha are fitted into respective canals to provide tug back, their color coded ends are seared off. The reference point where the cutting is done enables the specialist to confirm the proper working depth. The searing off of the color coded portion of the gutta percha can lead to confusion, since now there is no way to visually determine the size of the cone.

Once the master cones are inserted, a radiograph is taken to radio-graphically inspect the relationship of the master cones to the radiographic terminus of the roots. Assuming that radiographic findings and working lengths are all proper, the master cones are removed from all the canals and set aside. Typically they are placed somewhere on the bracket tray used by the dentist. Final irrigation of the canals and re-insertion of the master cones follows.

When the cones are placed on the bracket tray, it becomes difficult to know which cone goes in which canal, because their color-coded ends are seared off and because the different diameters of the cones are difficult to determine with the naked eye. Also, it is not uncommon to accidentally touch the master cones on the bracket table with another instrument; this too can lead to confusion. Further, the master cones should avoid touching any instruments previously used in the oral cavity which may have been contaminated with saliva; saliva must be kept out of the roots so as to avoid contamination. After irrigation and drying the canals with paper points, the master cones are coated with sealer of choice and cemented to working depth. Tops of master cones are then heated, condensed and spread through either lateral or vertical condensation, the latter being preferred. Accessory points are now inserted and further condensed until a dense three dimensional fill has been achieved.

The current invention addresses and eliminates the confusion that can arise from the time the master cones are removed from the tooth to the time they are replaced back into the tooth for final sealing.

DETAILED DESCRIPTION

Figure 1:
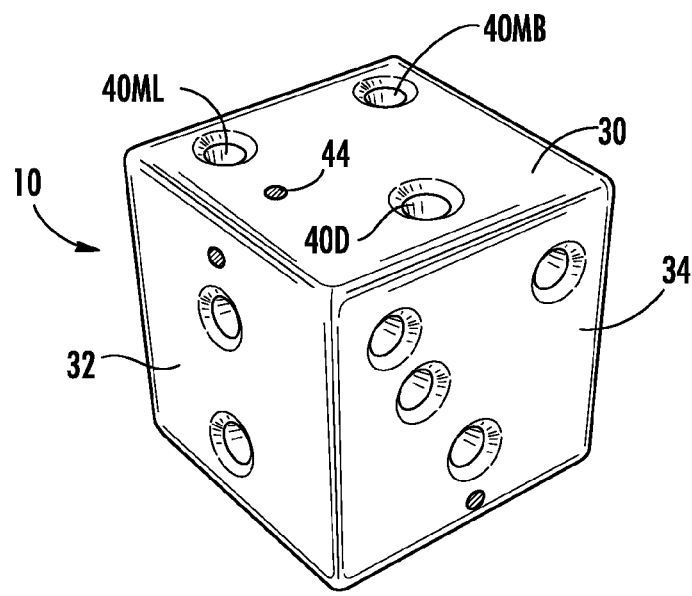
FIG. 1 is a top perspective view of a device that is a first embodiment of the invention.

The present invention relates to endodontic therapy, and more specifically to a device that is useful for the organization of workpieces used during an endodontic procedure. The invention is applicable to devices of varying constructions. As representative of the invention, FIG. 1 illustrates a device 10 that is a first embodiment of the invention.

The device 10 (described below in detail) is useful when a doctor is performing root canal surgery on the teeth of a patient. A typical set of lower teeth is illustrated schematically at 20 in FIG. 2. The set of lower teeth 20 includes up to 16 teeth, eight on each side of the tongue.

Within the mouth and relative to the teeth 22, four directions are determined—mesial, distal, buccal, and lingual. The mesial direction is a direction from the back of the mouth toward the tip of the tongue 22 (toward the front of the mouth or the lips). The distal direction is opposite the mesial direction, and is thus a direction from the tip of the tongue 22 toward the back of the mouth. The buccal direction is a direction from the center of the tongue 22 laterally outward toward the cheek; a buccal direction can be on either side of the centerline of the mouth. The lingual direction is a direction opposite the buccal direction, and is a direction laterally inward toward the centerline of the tongue 22; a lingual direction can be on either side of the mouth.

These four directions are relative to the location of each tooth in the mouth. That is, on opposite sides of the mouth, buccal and lingual will be in opposite directions. Thus, as one example, for two teeth located laterally directly opposite each other on the jaw, the lingual sides of the two teeth will face toward each other, while the buccal sides of the two teeth, will face way from each other.

Figure 2:
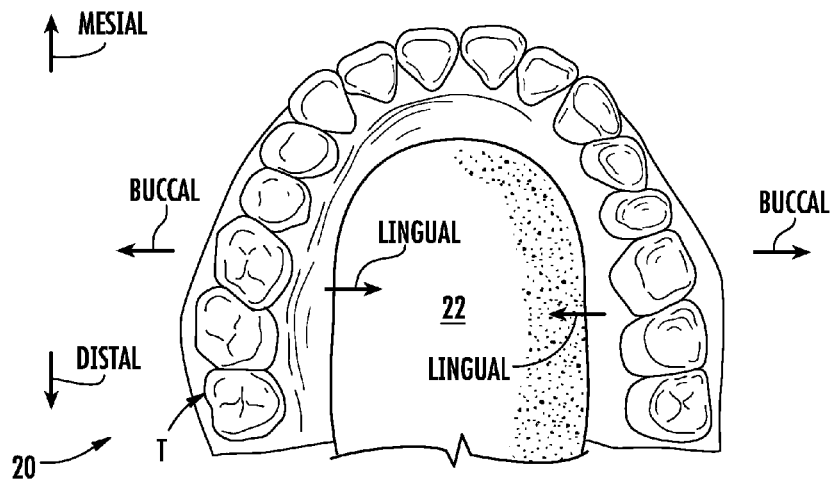
FIG. 2 is a schematic illustration of a set of lower teeth of a patient.

These four directions are illustrated in FIG. 2 and with respect to one particular tooth designated "T". The following description focuses initially on this tooth T as being representative of use of the device 10 as a first embodiment of the present invention. Later portions of this description address use of the device 10, and of other devices in accordance with the invention, on other teeth.

Figure 3:
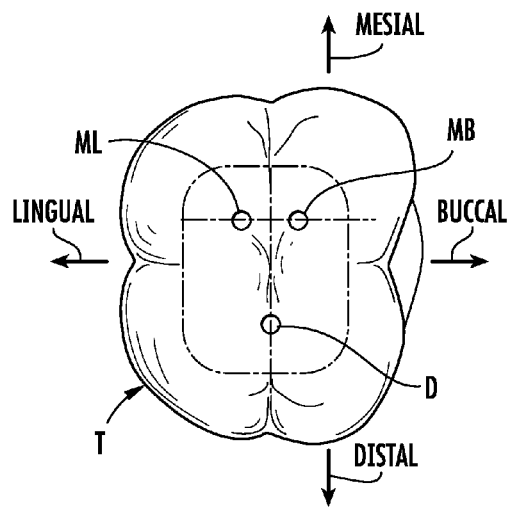
FIG. 3 is a representation of thee canals in one tooth.

In FIG. 3, the tooth T is shown as having three canals to be operated upon. The canals are designation ML, MB, and D. ML refers to mesial-lingual, and thus identifies the canal that is both mesial (toward the front of the mouth) and lingual (closer to the tongue 22 than to the cheek). MB refers to mesial-buccal, and thus identifies the canal that is both mesial (toward the front of the mouth) and buccal (closer to the cheek than to the tongue 22). D refers to distal, and thus identifies the canal that is the most distal of the three canals.

Figure 4:
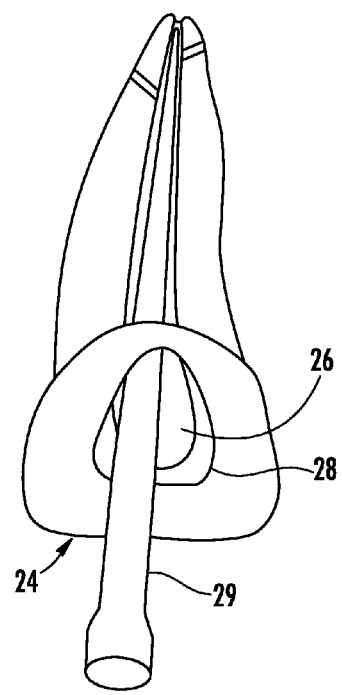
FIG. 4 is a schematic illustration of the use of a master cone in the canal of a tooth.

FIG. 4 shows schematically a typical tooth 24 having one canal 26. An access form 28 has been milled or otherwise formed to enable access to the canal 26. The canal 26 tapers towards its inner end (apex or apical terminus) and thus has a narrower inner end portion (apical constriction). A master cone 29 is shown inserted into the canal 26, before the outer end of the cone is sheared off.

Figure 7:
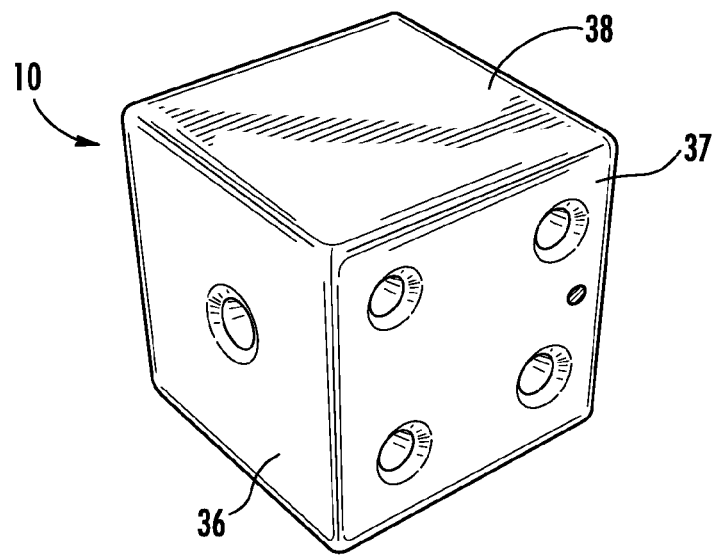
FIG. 7 is a bottom perspective view of the device of FIG. 1.

The device 10 is used in the organization of materials (workpieces) during the endodontic treatment of the three canals, ML, MB and D of the tooth T. The device 10 is a cube with three surfaces 30, 32, and 34 of its six surfaces total, visible in FIG. 1. FIG. 7 shows the remaining surfaces 36, 37 and 38 of the device 10, as discussed below.

The illustrated device 10 may be about one and one half inches on a side, and may be made from an autoclavable (sterilizable) material such as anodized aluminum. This size enables the provision of enough receptacles on each side, of a desired size, to handle any anticipated work. The device 10 may alternatively be made for single use, for example, through a plastic injection molding process, and thus be disposable.

There are three receptacles 40ML, 40MB, and 40D spaced apart from each other on the side surface 30 of the device 10 (which is uppermost when the cube is oriented on the table as shown, and is therefore referred to herein as the "upper side surface"). The receptacles receive and support the cones when they are temporarily out of the tooth. Each one of the receptacles is of a width and depth to safely contain and support a gutta percha cone, with its upper end portion projecting vertically above the surface 30 so that the doctor can readily grasp the cone by hand. A suitable depth for a receptacle may be in the range of from about 10 millimeters to about 30 millimeters, and preferably about 20 to 25 millimeters. The receptacles may be cylindrical as shown (having been drilled in metal), with a diameter in the range of from about three millimeters to about 9 millimeters, and preferably about 6 millimeters.

The device 10 includes an orientation marker 44 located on the upper side surface 30. The orientation marker 44 is located adjacent to one of the four edges of the device that bound the upper side surface 30. The orientation marker 44 may be a dot of a color different from the color of the device, or may be a dimple or indentation in the surface 30, or may be a protrusion above the surface, as but some additional non-limiting examples. Other examples are discussed below.

The orientation marker 44 is optional. Specifically, the device 10 may be used with the doctor remembering, during the course of a particular procedure, where the various cones go, aided by the fact that the receptacle pattern in the device mimics, or is a visual representation of, the canal pattern in the tooth. Thus, where the device does have a receptacle pattern that corresponds to the canal pattern, an orientation marker may not be necessary, although it may be helpful.

Figure 5:
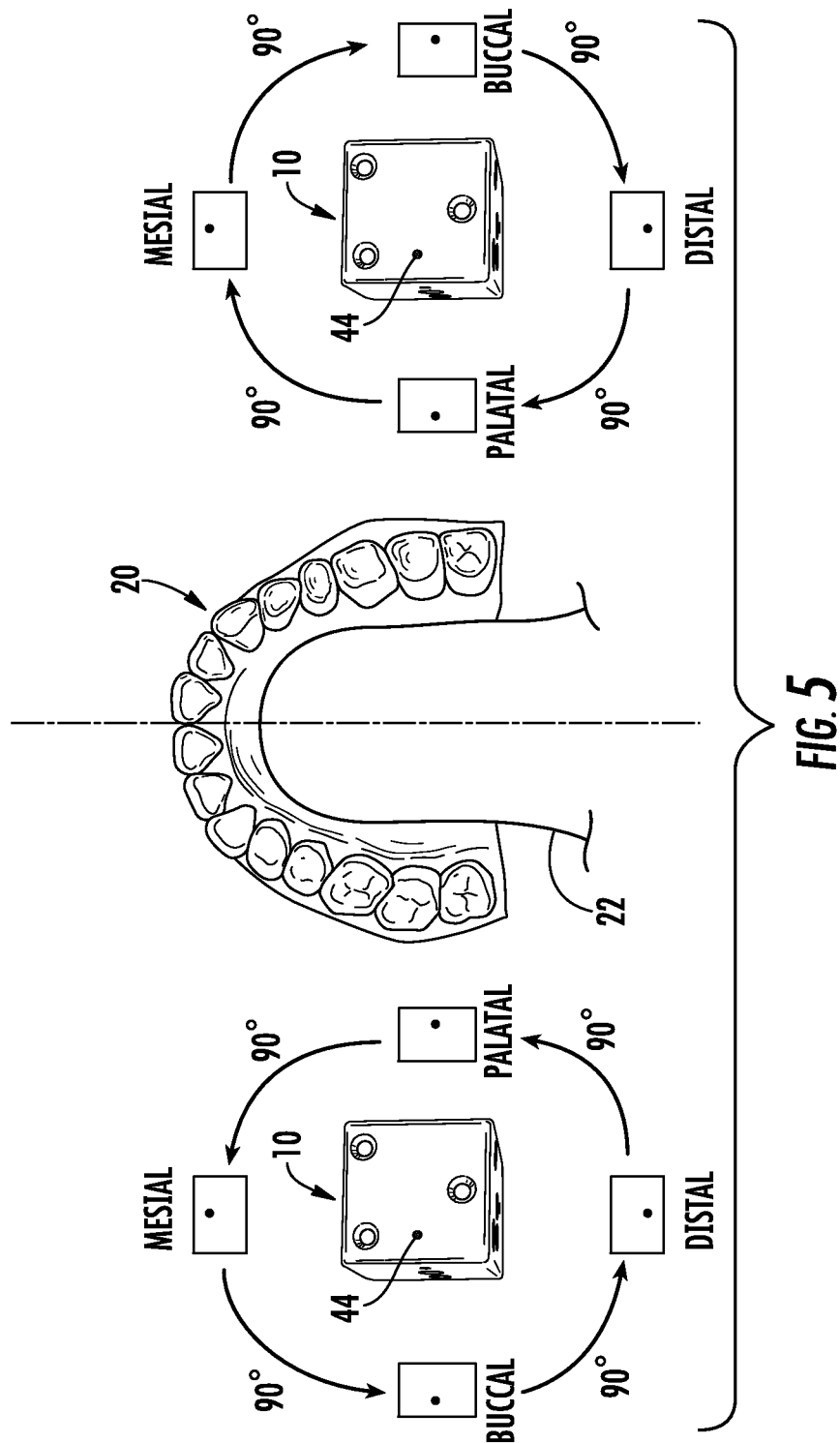
FIG. 5 is a schematic illustration of use of an orientation marker on a device of the present invention.

Use of the orientation marker 44 is illustrated schematically in FIG. 5. FIG. 5 shows schematically the patient's tongue 22 in the center of the illustration. The left portion of the illustration shows usage of the device 10 while working on a tooth that is on the left side of the mouth. The right portion of the illustration shows usage of the device 10 while working on a tooth that is on the right side of the mouth. In each case, the orientation marker 44 of the device 10 is selected (by convention of the doctor) to indicate one of the four above-identified directions—palatal (lingual, mesial, buccal, or distal.

Because different teeth can have different numbers of canals, arranged in different spacing/arrangements across the surface of the tooth, the different sides of the device 10 have different numbers and arrangements of receptacles. For example, in the device 10 shown in FIG. 1, the side 32 has two receptacles. The side 34 has four receptacles, arranged in a different pattern from the three receptacles on the upper side surface. The remaining three sides 36, 37 and 38 of the device 10, as shown in FIG. 7, have one, four, and zero receptacles, respectively. Side 37 includes its own orientation marker, located adjacent one of the four edges that form the boundaries of the side. The one side 36 that has only one receptacle does not have an orientation marker (although it could); it is not strictly necessary since there is only one receptacle.

Figure 6:
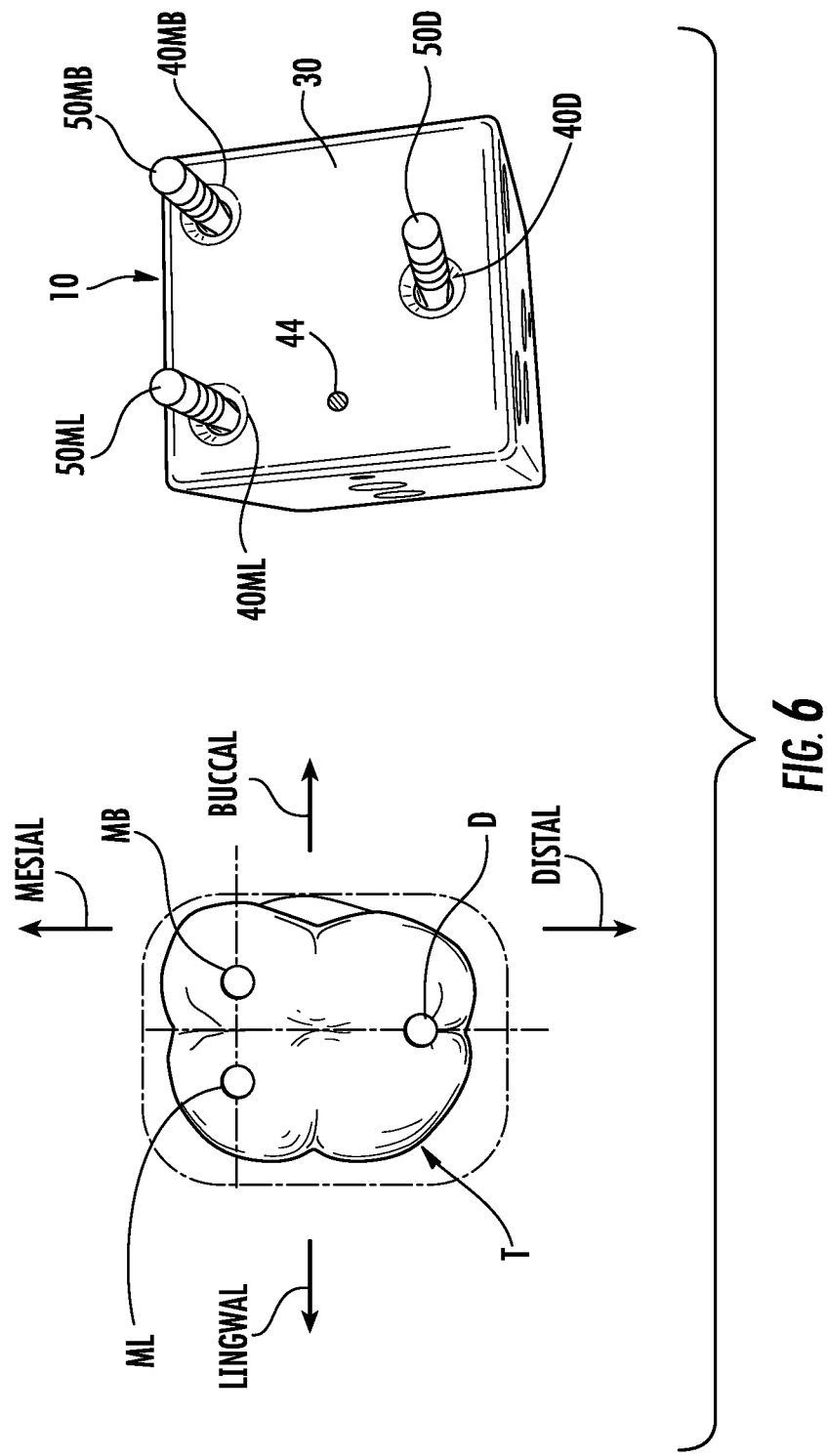
FIG. 6 is a schematic illustration of use of the device of FIG. 1 in performing a procedure on the tooth of FIG. 3.

FIG. 6 illustrates schematically the use and orientation of the device 10 relative to the tooth T. At the commencement of the endodontic procedure, the doctor selects a side of the cube 10 that has a receptacle pattern corresponding to (matching, or that is a visual representation of) the canal pattern in the tooth T. The doctor makes a determination as to how the orientation marker 44 is to be used—for example, to indicate a lingual direction. Then, when the cones are removed from the tooth as described above, they are placed in the corresponding receptacles in the device 10, based on the location of the receptacle pattern and the orientation marker 44. The orientation marker 44 tells the doctor how to orient the device so that the doctor knows which receptacle (and its received cone) is associated with which canal.

Thus, depending on the convention chosen by the doctor, the marker 44 can serve to designate check side (buccal) or mesial (front) or distal (back). In the illustrated embodiment, the marker 44 indicates a lingual direction (laterally inward toward the tongue). The device 10 is shown as having three cones in its three receptacles 40ML, 40MB, and 40D in the upper side surface 30; the three cones are designated 50ML, 50MB, and 50D, corresponding to the three canals ML, MB, and D in the tooth T. The cones 50ML, 50MB, and 50D have a one-to-one relationship with the canals ML, MB, and D and with the receptacles 40ML, 40MB, and 40D.

The receptacle pattern acts as a template for, or representation of, the canal pattern in tooth T on the surface 30. The receptacle pattern is a visual representation of the canal pattern in the tooth T. As a result, the doctor can remove the cones 50ML, 50MB, and 50D from their particular locations ML, MB, and D in the tooth T, and place them into the corresponding receptacles 40ML, 40MB, and 40D in the cube 10, knowing which cone goes with which canal, and that correlation between cone and canal and receptacle will persist throughout the procedure. The cones stay in the one-to-one relationship with the canals from which they were removed.

Figure 8:
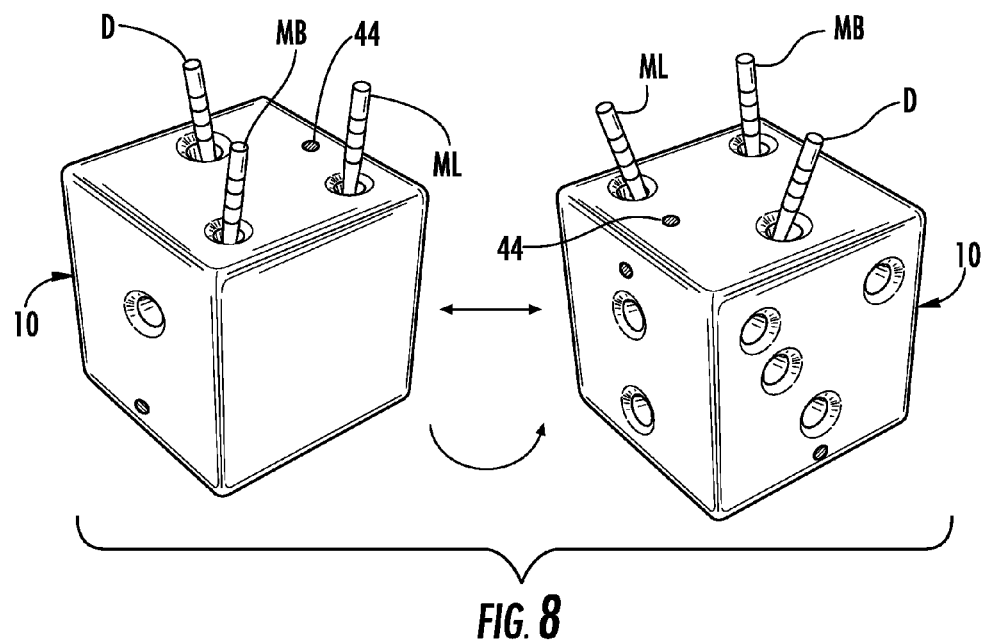
FIG. 8 is a schematic illustration showing movement and reorientation of the device of FIG. 1.

Because the orientation marker 44 indicates a particular direction that is known to the doctor, and because the doctor knows which tooth is being worked on, the device 10 can, as illustrated schematically in FIG. 8, be placed anywhere on the bracket tray or other support surface, and can even be rotated about its vertical axis, without causing a problem. The arrows in FIG. 8 illustrate rotational and translational movement of the device 10 from its original position (to the left as viewed in FIG. 8). To a secondary or unintended position (to the left as viewed in FIG. 8). The cones 50ML, 50MB, and 50D stay in their original positions in the device 10, without moving relative to each other, and so the doctor always knows which cone goes with which canal. Whenever the device is misoriented as shown in FIG. 8, it can be reoriented easily because of the presence of the orientation marker 40.

Thereafter, when it is time to reinsert the cones 50ML, 50MB, and 50D into the tooth T, the doctor pulls the cones out of the device receptacles 40ML, 40MB, and 40D one at a time, and puts them in the corresponding canals ML, MB, and D, respectively. Until that happens, the cones (1) are correctly associated with their respective canals, and are not mixed up with each other; (2) are not lost, because they are securely received in the receptacles in the cube; and (3) are not on a work surface where they might be subject to contamination from other tools or instruments. The cube shape of the device 10 allows each face of the cube to represent one typical orifice configuration encountered during endodontic treatment. These are all advantages and benefits of a device of the present invention.

The orientation marker 44 typically is used to represent the palatal aspect (lingual) of a tooth, when working on one tooth. However, the orientation marker serves as a matter of convention designated by the dental specialist, and so it can alternatively serve to designate other orientation positions, for example, when working on multiple teeth.

As noted above, the optional orientation marker can take many forms. Some examples are listed above. As additional examples, the orientation marker can be intruded demarcation of any shape or depth in the surface of the device. Alternatively, the orientation marker can be a through hole that extends through the entire device. Further, the orientation marker can be a screw type insert in a threaded drilled hole or recess. The screw is preferably of a different color from the cube so that it stands out visually. The screw preferably has a flat head that is flush with the surface. In that way, various marker screws on the sides of the device would not interfere with the ability of the device to stay flat on the bracket tray. Still further, the marker can be a laser marked or engraved symbol. As is apparent from the drawings, the particular side 36 of the device 10 having only one receptacle does not have an orientation marker, since orientation is not necessary when working on only one canal.

The receptacles on a device of the present invention themselves can each be surrounded by an outline color for easier viewing. In addition, the entire outline form of proper access shape for the canals of a tooth can be intruded several millimeters into the device body along with the rounded receptacles; this in effect will remind the doctor of proper outline form during the access preparation of a tooth (see FIG. 12 as an example). Thus, the placement of the receptacles within the outline form correspond to the location or the canals within the tooth. The device can also include one or more cross drilled through channels (for example, as designated at 76 in FIG. 11), for faster cooling after being autoclaved. The receptacles which hold the gutta perchas can be tapered or straight. The inner end of each receptacle can taper to an apex at the base of the receptacle.

As another example of usage of a device of the present invention, the cube 10 can be used when working simultaneously on two teeth with two canals each, or when working on two teeth where one tooth has one canal, and the other tooth has two canals. As one example, when working on a first tooth having one canal only and a second tooth having two canals, the doctor can use a cube side that has three receptacles. When that occurs, the doctor need to remember which cone/receptacle combination is associated with which tooth; the orientation marker can be of assistance.

Figure 9:
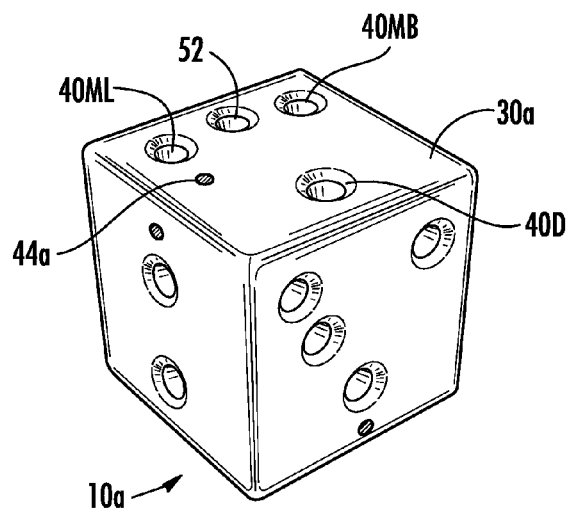
FIG. 9 is a top perspective view of a device that is another embodiment of the invention.

FIG. 9 illustrates a variation of the basic cube concept which takes into account the fact that lower molars often have a third canal between the two mesial canals, or a third canal between the two distal canals. In this case, a modified device 10A is provided that has an additional receptacle 52 on its upper surface 30A. This additional receptacle 52 can be used to receive and support the additional cone that is needed for the extra canal. And, this device 10A can still be used for a three canal tooth as above with respect to the tooth T, because the extra receptacle does not interfere with the above-described procedures.

Figure 10:
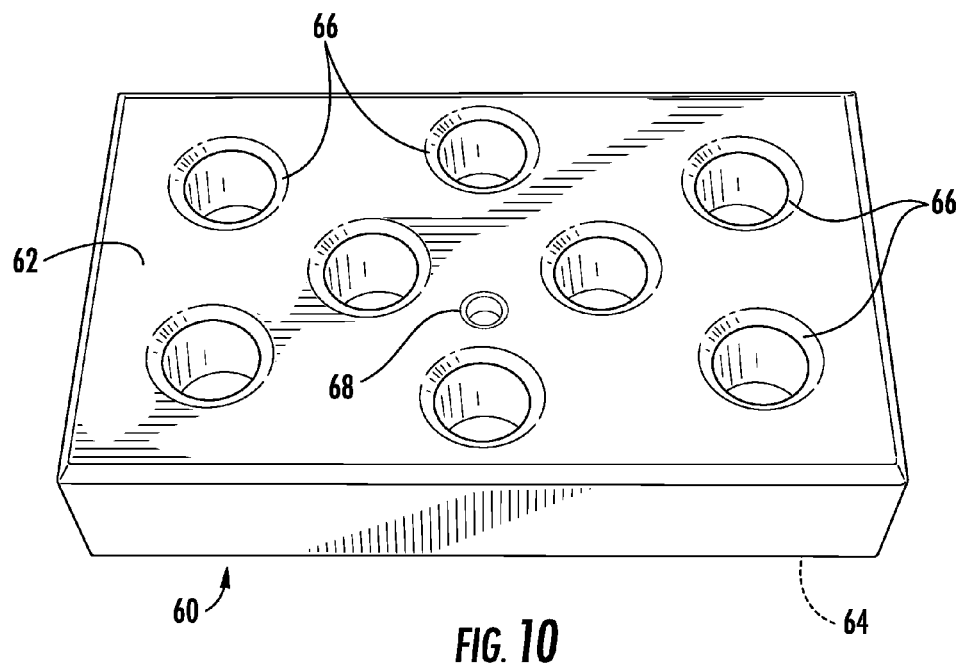
FIG. 10 is a top perspective view of a device that is another embodiment of the invention.

The invention can be embodied in devices other than a cube-shaped device such as the device 10. As one example, in a second embodiment, the device 60 (FIG. 10) is a flat block having a generally rectangular configuration with an upper side surface 62 and a lower side surface 64. The block 60 is shorter in height than the cube 10 but is longer in length. The block 62 has receptacles 66 on only the upper side surface 62.

The block 60 has a large number of receptacles 66, so that it can accept up to six or more cones. The receptacles 66 are arranged in a uniform pattern, rather than in a pattern that matches a typical tooth canal pattern. Therefore, the doctor can use the device 60 for any one tooth, without flipping it over, since it has at least as many receptacles 66 as are present on any one side of the cube 10. Specifically, the doctor can select one or more receptacles 66 that form a pattern that is visual representation of the pattern of the canals in the tooth being worked upon. The doctor can also use the device 60 to work on two teeth simultaneously, because of the large number of receptacles 66. The device 60 also has an orientation marker 68, which can serve to specify directional orientation such as palatal (lingual), buccal (facial), mesial or distal.

Figure 11:
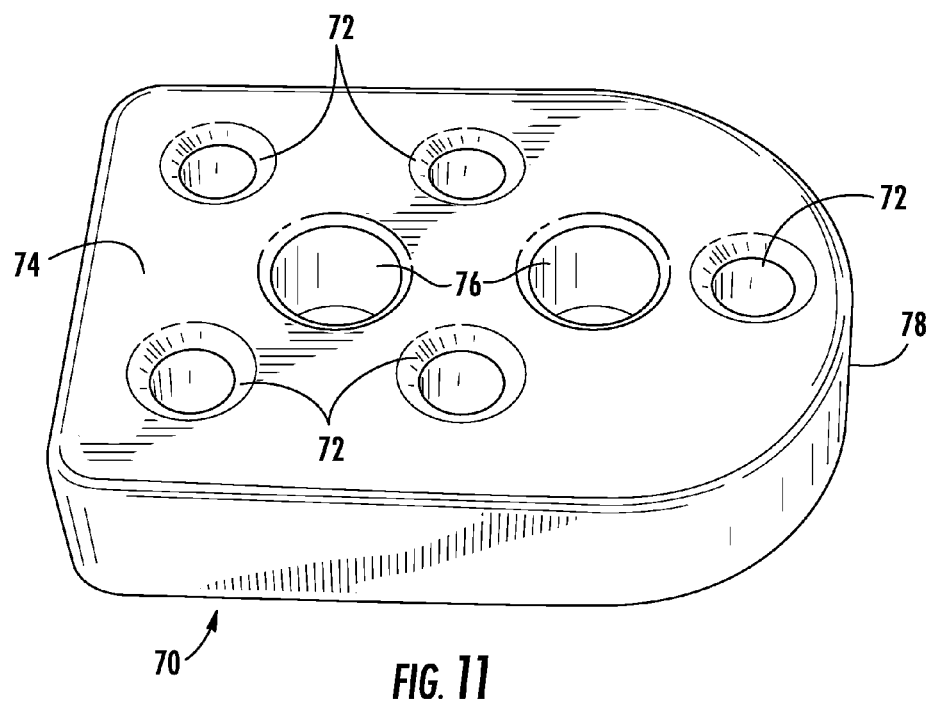
FIG. 11 is a top perspective view of a device that is another embodiment of the invention.

FIG. 11 illustrates a device 70 that is a third embodiment of the invention. Like the device 60 (FIG. 10), the device 70 is a flat block, lower than the cube 10, having receptacles 72 on only its upper side surface 74. The receptacles 72 are arranged in a uniform pattern, rather than in a pattern that matches a typical tooth canal pattern. The device has five receptacles, so it can accept up to five cones. Thus, the doctor can use the device 70 as a substitute for any one of the six sides of the cube 10, for any one tooth, without flipping the device over. In addition, two through holes 76 are provided to enable faster cooling after the autoclaving (sterilization) cycle is complete. The specific receptacles 72 to be utilized during the procedure (out of the five total) are selected to mimic the pulp chamber morphology and its respective orifices, once access into a particular tooth has been gained. The device 70 has a rounded end 78 that serves as an orientation marker.

Figure 12:
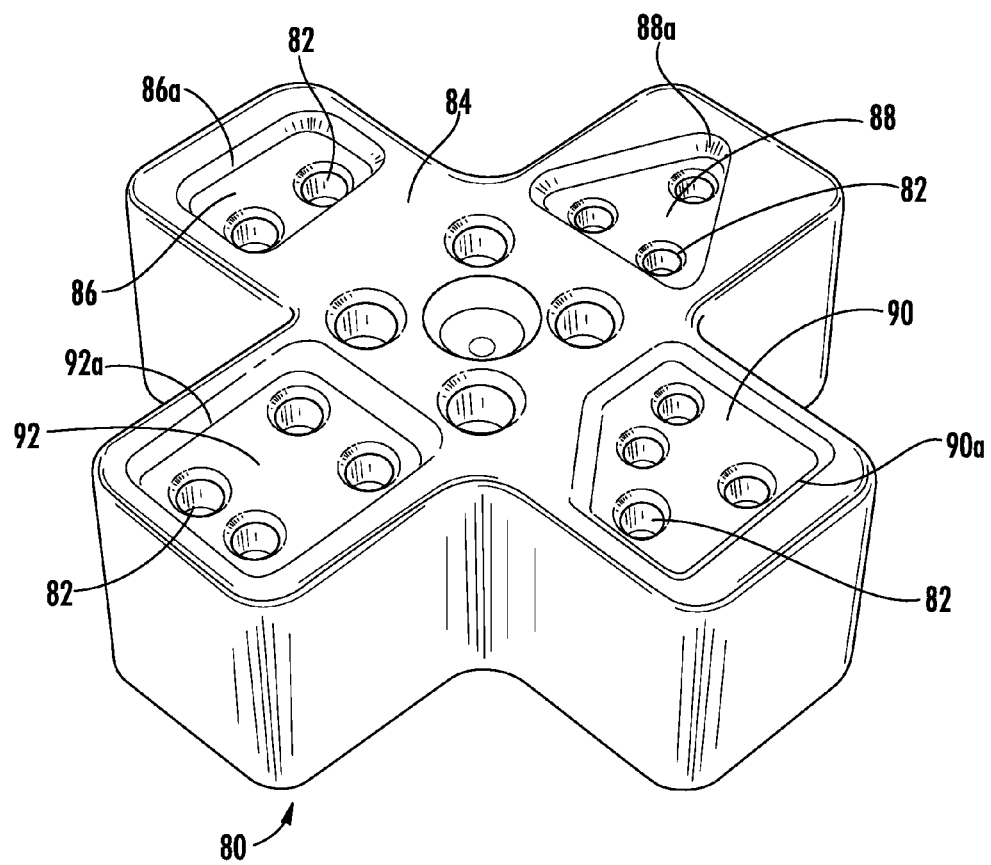
FIG. 12 is a top perspective view of a device that is another embodiment of the invention.

FIG. 12 illustrates a device 80 that is a fourth embodiment of the invention. Like the devices 60 and 70 (FIGS. 10 and 11), the device 80 has receptacles 82 on only its upper side surface 84. The device 80 is cruciform in configuration, with four distinct receptacle patterns 86, 88, 90, and 92, one on each arm of the cross. In each one of the four receptacle patterns 86-92, the receptacles 82 are arranged in a pattern that mimics or matches a typical tooth canal pattern. Thus, the doctor can select an appropriate receptacle pattern 86-92 that is pre-identified, on one side of the device 80, as compared to selecting individual receptacles on one particular side of the device.

Further, as discussed above, the entire outline form 86a, 88a, 90a, and 92a of proper access shape for a tooth is formed on each arm of the cross, around the respective receptacle pattern 86, 88, 90, and 92. This form 86a-92a can be extruded (projecting above the upper side surface 84 of the cross) or can alternatively be intruded several millimeters into the device body along with the receptacles. This in effect will remind the doctor of proper outline form during the access preparation of a tooth, thus serving as an orientation marker.

In the device 80, a central receptacle 94 can be used when working on a tooth that has only one canal. The four receptacles 96 that surround the central receptacle 94 can be used to hold paper points of assorted sizes, or accessory gutta percha points that get condensed into a tooth canal after the master cones are cemented.

The invention also relates to a method. Specifically, the invention relates to a method for use in performing an endodontic procedure on a tooth of a patient. The procedure includes the use of workpieces (e.g., the cones) that are placed in canals of the tooth.

The method includes the step of providing a holder having a lower side surface for resting on a support surface such as a dental tray. The holder has an upper side surface with receptacles configured to receive and support the workpieces at a location off the support surface and in a generally vertical orientation with upper end portions of the workpieces projecting upward out of the receptacles. The receptacles are arranged in a pattern that is a visual representation of the canal patter in the tooth with the receptacles corresponding in a one-to-one relationship with the canals.

The method also includes the steps of inserting the workpieces in a one-to-one relationship into the canals of the tooth, and removing the workpieces from the canals of the tooth. The method further includes the step of placing the workpieces in the receptacles in the holder to store the workpieces off the support surface while the workpieces are out of the tooth, including creating a one-to-one relationship between the workpieces and their respective receptacles and their respective canals.

The method also includes the steps of removing the workpieces form the receptacles when the workpieces are to placed in the canals, and inserting the workpieces into the canals of the tooth, including maintaining the one-to-one relationship between the workpieces and the canals.

The step of providing a holder may include providing a holder having an orientation marker for orienting the holder to align the holder with the canal pattern in the tooth. The method may further include the step of orienting the holder on the support surface relative to the tooth by means of the orientation marker.

From the above description of the invention, those skilled in the art will perceive improvements, changes and modifications. For example, the configuration of the sides of the cube can have any order. Also, the cube can be made large enough so that opposing receptacles do not interfere with each other. Also, another embodiment would be to take all the sides of the cube in line with each other on a flat device like those in FIGS. 10-12. Such improvements, changes and modifications within the skill of the art are intended to be covered by the appended claims.

The invention claimed is:

1. A holder for temporarily holding dental workpieces when the workpieces are not placed in a tooth during an endodontic procedure, the holder comprising:

a plurality of receptacles, each comprises a receptacle opening disposed on external surfaces of the holder for receiving the workpieces therein said plurality of receptacles; each of said plurality of receptacles extends from its respective receptacle opening and partially through the holder, thus having a bottom within the holder; each of said plurality of receptacles is dimensioned and shaped for securely holding a workpiece with an end of said workpiece protruding from the holder;

the receptacle openings are arranged on the external surfaces of the holder such that at least three of said external surfaces each exhibits one of three different visual representations formed by the receptacle openings corresponding to three different common patterns of root canal orifices in a coronal pulp chamber;

wherein a first surface of said at least three of said external surfaces exhibits a first visual representation of said three different visual representations, said first visual representation consists of only four receptacle openings arranged in a generally rectangular pattern on said first surface, corresponding to a first common pattern of said three different common patterns of root canal orifices in a coronal pulp chamber;

a second surface of said at least three of said external surfaces exhibits a second visual representation of said three different visual representations, said second visual representation consists of only four receptacle openings arranged in a generally triangular pattern on said second surface, corresponding to a second common pattern of said three different common patterns of root canal orifices in a coronal pulp chamber; and a third surface of said at least three of said external surfaces exhibits a third visual representation of said three different visual representations, said third visual representation consists of only three receptacle openings arranged in a generally triangular pattern on said third surface, corresponding to a third common pattern of said three different common patterns of root canal orifices in a coronal pulp chamber.

2. The holder according to claim 1, further includes an orientation marker on at least one of said external surfaces of the holder, so as to indicate one of a lingual, mesial, buccal, and distal direction.

3. The holder according to claim 2, wherein said orientation marker is selected so as to provide an asymmetric visual appearance to said at least one of said external surfaces.

4. The holder according to claim 1, wherein the holder is a substantially rectangular prism having six sides, three of said six sides each comprising each of said at least three external surfaces.

5. The holder according to claim 4, wherein said prism is a cube about one and one half inches a side.

6. The holder according to claim 1, wherein the holder is autoclavable.

7. The holder according to claim 1, wherein the holder is made for single use and is thus disposable.

8. The holder according to claim 1, wherein the holder further comprises at least one through hole to enhance heat transfer into and out of the holder.

9. The holder according to claim 1, wherein the holder comprises four arms, three of said four arms each comprising each of said at least three external surfaces.

10. A method of utilizing a holder for temporarily holding dental workpieces during an endodontic procedure on a tooth, the method comprising:

providing a holder;

said holder comprising a plurality of receptacles for temporarily holding the workpieces when the workpieces are not placed in a tooth during the endodontic procedure; each of said plurality of receptacles comprises a receptacle opening disposed on external surfaces of the holder for receiving the workpieces therein said plurality of receptacles; each of said plurality of receptacles extends from its respective receptacle opening and partially through the holder, thus having a bottom within the holder; each of said plurality of receptacles is dimensioned and shaped for securely holding one workpiece of said workpieces with an end of said one workpiece protruding from the holder;

the receptacle openings are arranged on the external surfaces of the holder such that the external surfaces exhibit visual representations formed by the receptacle openings corresponding to common patterns of root canal orifices in a coronal pulp chamber;

determining an external surface from said external surfaces that exhibits a visual representation formed by the receptacle openings best matches a pattern of root canal orifices in a coronal pulp chamber of the tooth having the endodontic procedure;

placing the holder on a support with the determined external surface facing upward and aligning the holder such that the determined external surface corresponds in lingual, mesial, buccal, and/or distal direction with the tooth having the endodontic procedure;

inserting workpieces into root canals of the tooth having the endodontic procedure;

removing the workpieces from the root canals; and storing the workpieces temporarily in corresponding receptacles having respective receptacle openings arranged on the determined external surface, including creating and maintaining a corresponding relationship among the workpieces, the corresponding receptacles, and the root canals base on the matching visual representation of the determined external surface and the pattern of root canal orifices in the coronal pulp chamber of the tooth having the endodontic procedure, such that the workpieces are temporarily stored in said corresponding receptacles corresponding to the root canals from which the workpieces were removed.

11. A method according to claim 10, wherein the corresponding relationship between the corresponding receptacles and the root canals of the tooth having the endodontic procedure is a one-to-one relationship.

12. A method according to claim 10, wherein the holder further includes an orientation marker on at least one of said external surfaces, as to indicate one of a lingual, mesial, buccal, and distal direction; and wherein the step of aligning the holder further includes orienting the holder base on said orientation marker.

* * * * *